United States Patent [19]

van der Heijden

[11] 4,382,548

[45] May 10, 1983

[54] DISPENSER FOR AIR-TREATING VAPORS

[76] Inventor: Joahnnes van der Heijden, 61 Collingwood Crescent, Guildford, Surrey, England

[21] Appl. No.: 281,812

[22] Filed: Jul. 9, 1981

[51] Int. Cl.³ .......................... A61L 9/12; B65D 43/00
[52] U.S. Cl. ........................................ 239/56; 220/87; 220/282; 239/58
[58] Field of Search .............................. 239/35, 53–60; 220/87, 281, 282

[56] References Cited

U.S. PATENT DOCUMENTS

| 2,830,845 | 4/1958 | Cottle | 239/56 X |
| 3,504,821 | 4/1970 | Wolbers | 220/282 |
| 4,014,501 | 3/1977 | Buckenmayer | 239/58 |

FOREIGN PATENT DOCUMENTS

| 57270 | 12/1952 | France | 220/282 |

Primary Examiner—Andres Kashnikow

[57] ABSTRACT

A dispenser for air-treating vapors of the type having lower and upper members adjustable to different vertically spaced positions to control the dispensing of air-treating vapors. The invention includes a lever hinged at one end to the upper member and having a depression surface at its opposite end and further having a lower fulcrum in contact with the lower member midway between the lever ends. The lever serves to raise the upper member to open the device for vapor-dispensing. The fulcrum is preferably a convex cam about which the lever rotates during depression. Certain preferred embodiments include various interacting elements on the lever and the lower member or on the upper and lower members to control and limit the raising of the upper member. In preferred embodiments the hinge is centrally located to provide a generally central lift point for the upper member.

10 Claims, 5 Drawing Figures

DISPENSER FOR AIR-TREATING VAPORS

FIELD OF THE INVENTION

This invention relates to devices for dispensing air-treating vapors. More particularly, the invention relates to container-dispensers having two interengaged portions which may be adjusted to different vertically spaced positions to control the dispensing of air-treating vapors.

BACKGROUND OF THE INVENTION

Vaporizable air-treating materials, such as cardboard, fibreboard, or other fibrous carriers soaked with volatile liquids, provide an effective means for gradual introduction into the air of air-treating vapors, including vapors used for air freshening or the killing of insects. In the packaging of these volatile materials, it is desirable to utilize dispensers which provide adequate retention of the volatiles while effectively controlling the rate of their evaporation and the dispensing of air-treating vapors during use. Other desirable characteristics for dispensers of air-treating vapors are simplicity in construction and operation and attractiveness in appearance.

A wide variety of such dispensers for air-treating vapors have been developed, including the dispensers disclosed in U.S. Pat. Nos. 2,765,950; 2,830,845; and 4,014,501. Such dispensers of the prior art have varying advantages and disadvantages. Some may be difficult to operate, requiring, for example, two hands for adjustment or a period of learning for operation. Some, because of various mechanical requirements, impose design limitations which are harmful to product aesthetics. A need remains for a superior, easily operated air freshener of the type having two principal interengaged portions which are adjustable to different vertically spaced positions with respect to each other to control dispensing.

BRIEF SUMMARY OF THE INVENTION

An improved device for dispensing air-treating vapors is provided, such device being of the type having two relatively adjustable parts the relative positions of which control the rate of emission of vapors from a volatile material contained therein.

The dispenser of this invention has a lower member with an open top and an upper member with an open bottom, the upper and lower members being nested together. The upper member, often referred to herein as an insert, is preferably nested within the lower member, often referred to herein as a shallow dish. The upper member is movable with respect to the lower member between a fully nested position enclosing a volatile air-treating material and a raised postion exposing the volatile material to the surrounding atmosphere. An important characteristic of this invention is a lever which is hinged at one end to the upper member and has an upper depression surface at its opposite end and a lower fulcrum in contact with the lower member midway between the lever ends. When an operator depresses the lever, by applying finger pressure to the upper depression surface, the lever rotates about its fulcrum to raise the upper member from its fully nested position to its raised position. Lifting pressure is applied to the upper member through the hinge by the lever motion.

The shallow dish has a bottom and a surrounding upstanding wall. The insert, which is nested within the dish, has a cover and a plurality of sidewall segments extending downwardly therefrom and adjacent to the upstanding wall of the dish. The sidewall segments define apertures therebetween which allow air flow through the dispenser when the insert is in an elevated position. The cover defines an opening within which the lever is located. The insert, lever, and the hinge therebetween are preferably an integral plastic piece.

The lever is preferably located such that its depression surface is adjacent to the wall of the lower dish member and its hinge is remote from the wall in a generally central position to provide a substantially centrally located lift point for the insert. In a highly preferred embodiment, the fulcrum is formed as a convex cam about which the lever rotates as it is depressed. Such convex cam slides on the bottom of the dish as the lever is depressed, the fulcrum point moving along such convex cam away from the hinge as depression, and the resultant insert elevation, progresses.

In a preferred embodiment, the shallow dish bottom has a raised portion engaging the cam and the cam has a stop at the end of the cam which is most remote from the hinge. The stop is engageable with the raised portion to prevent further depression of the lever when the insert reaches its fully raised position.

In a preferred embodiment, the depression surface of the lever is substantially coplanar with the cover. It is also preferred that the sidewall segments of the insert and the upstanding wall of the dish have interacting means to prevent raising of the insert beyond its fully raised position, that is, to prevent complete disengagement of the lower and upper members.

A volatile air-treating material will be located between the bottom of the shallow dish and the cover of the insert. The form of such volatile air-treating material and its exact location within the dispenser may be varied. However, it is preferred that the volatile material be suspended beneath the cover on support means formed on the sidewall segments. The volatile material may be in the form of an impregnated fibreboard piece cut to fit within the dispenser.

The dispenser of this invention will typically have the appearance of a shallow dish sitting on a horizontal surface. The dispenser is intended for placement on a variety of surfaces throughout the house, such as tabletops, kitchen counters, and bathroom counters.

When the insert member is fully nested within the dish member, little or no air-treating vapor will escape. To open the device, the operator simply depresses the lever depression surface, an operation which can be carried out with a finger of one hand. Such action raises the insert to whatever extent may be desired, exposing the side apertures to air flow. The outflow of air-treating vapors will be maximized if the insert is in its fully raised position. The rate of vapor dispensing will be lower, however, if the insert is only partially raised. When the operator desires to reduce the vapor output or close the dispenser, he simply pushes down on the insert cover portion until the insert is at the desired elevation or is fully nested with the dish member.

OBJECTS OF THE INVENTION

It is an object of this invention to provide an improved dispenser for air-treating vapors.

Another object of this invention is to provide an improved vapor dispensing device of the type having two interengaged portions relatively adjustable to different vertical positions to control the dispensing of vapors from a volatile material contained therein.

Another object of this invention is to provide a simple vapor-dispensing device which may be operated with one hand.

Still another object of this invention is to provide a vapor dispenser which imposes fewer constraints on design than certain dispensers of the prior art.

These and other objects of the invention will be apparent from the following descriptions of preferred embodiments.

DESCRIPTION OF PREFERRED EMBODIMENTS

Figure 1:
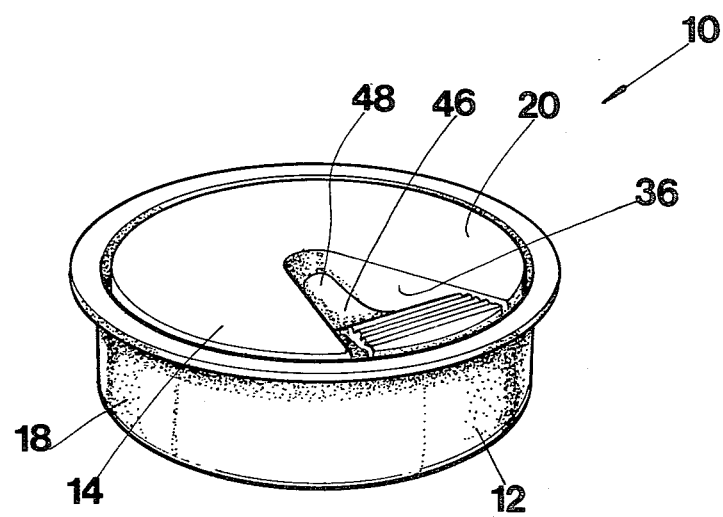
FIG. 1 is a persective view of the dispenser of this invention in the closed, fully nested condition.
Figure 2:
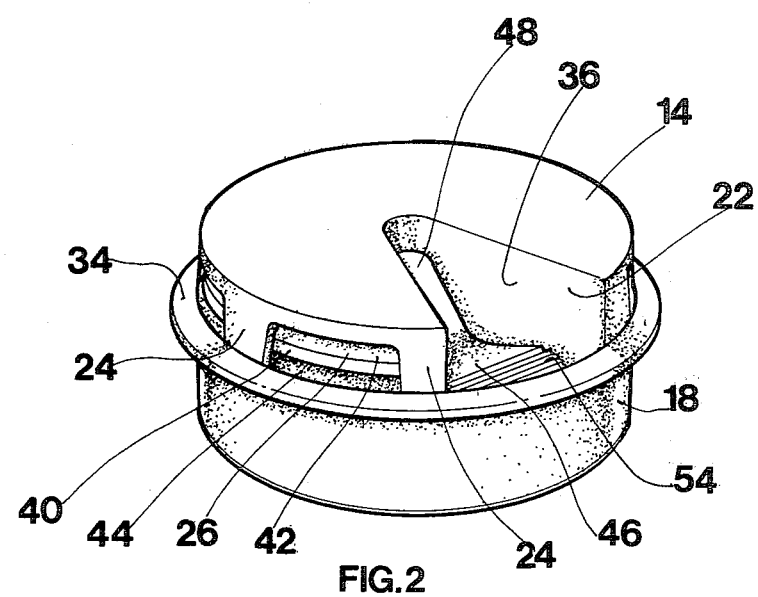
FIG. 2 is a perspective view as in FIG. 1, but showing the dispenser in its open condition.
Figure 3:
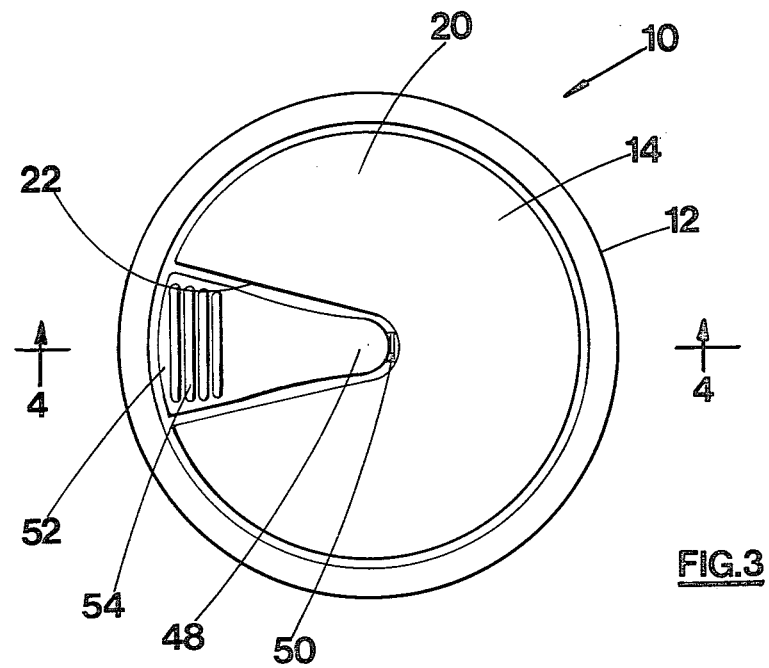
FIG. 3 is a top view of the device of FIG. 1.
Figure 4:
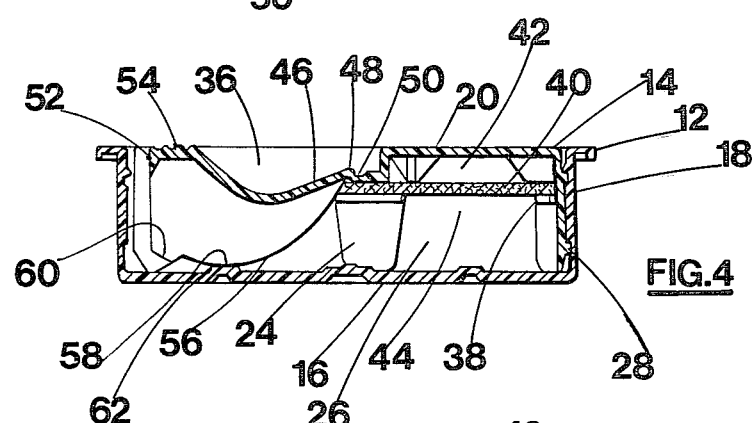
FIG. 4 is a side sectional view taken along Section 4—4 as indicated in FIG. 3.
Figure 5:
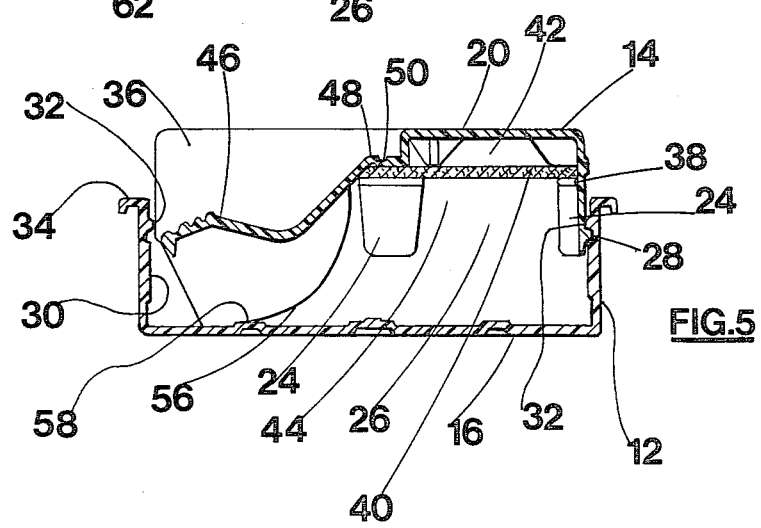
FIG. 5 is a side sectional view as in FIG. 4, but showing the dispenser in its opened condition.

Shown in the drawings is a dispenser 10 which is a preferred embodiment of this invention. Dispenser 10 has two principal parts, including a shallow dish 12 and an insert 14. Insert 14 is nested within dish 12. FIGS. 1 and 4 illustrate dispenser 10 in its closed, fully nested condition. FIGS. 2 and 5 illustrate dispenser 10 in its open, fully raised (or elevated) position. Insert 14 is vertically adjustable with respect to dish 12 between the closed and open positions.

Shallow dish 12 has a bottom 16 and a surrounding upstanding wall 18. Bottom 16 is substantially planar and in a horizontal orientation when dispenser 10 is in its normal position. Wall 18 extends substantially vertically upwardly from the edge of bottom 16. The lower member or dish 12 has an open top. The term "shallow," as used in describing dish 12, indicates that wall 18 is small in its vertical dimension compared to the horizontal dimension of bottom 16.

The upper member or insert 14 has a generally horizontal cover 20 and a plurality of sidewall segments 24 extending downwardly from the peripheral edges of cover 20. The sidewall segments 24 define apertures 26 between their adjacent pairs. Sidewall segments 24 are adjacent to upstanding wall 18 and have outwardly extending beads 28 on their outer surfaces which engage the inner surface 30 of upstanding wall 18 to hold insert 14 in whatever position of elevation the operator might select. Inner surface 30 has an inwardly extending annular bead 32 near the upper edge 34 of wall 18. Annular bead 32 and beads 28 are interacting means to prevent raising of insert 14 beyond its fully raised position, illustrated in FIGS. 2 and 5.

Cover 20 defines a lever opening 22 in which a lever 46 is located, as will be described in detail hereinafter. Although the major portion of cover 20 is parallel to bottom 16 of shallow dish 12 (i.e., horizontal), cover 20 also includes a downwardly extending skirt portion 36 around lever opening 22. Thus, insert 14 serves to prevent excessive loss of vapors from dispenser 10 when insert 14 is fully nested in dish 12.

Sidewall segments 24 have ledges 38 on their inner surfaces which form a means to suspend a layer of volatile air-treating material beneath the horizontal major portion of cover 20. Volatile air-treating material 40 is a fibreboard piece impregnated with a vaporizable air-treating composition. Air-treating material 40 is cut to fit under the horizontal portion of cover 20 on ledges 38 of sidewall segments 24. Ledges 38 are positioned such that there is an air space 42 above volatile material 40 and an air space 44 below material 40. The vaporizable composition used in material 40 may be any of a wide variety of air-treating compositions, including perfumes, deodorants, or insecticides. The air-treating material may be suspended or held within the dispenser of this invention in a variety of other ways.

Lever 46 is hinged at a first end 48 to cover 20 by a hinge 50. At the opposite end 52 of lever 46 is an upper depression surface 54 which is substantially coplanar with the major portion of cover 20. Depression surface 54 may be depressed by the operator's finger to raise insert 14 and thus open dispenser 10. Lever 46 has a lower convex cam 56 in contact with the annular raised portion 58 of bottom 16 of dish 12. Cam 56 forms a lower fulcrum about which lever 46 rotates as upper depression surface 54 is depressed. As upper depression surface 54 is depressed, the lever action exerts an upward pressure on insert 14 through hinge 50.

Lever 46 is positioned with respect to insert 14 such that upper depression surface 54 is adjacent to wall 18 and hinge 50 is remote from wall 18. Such positioning allows the lifting action of lever 46 to be exerted on insert 14 at a substantially centrally located point. This allows insert 14 to be lifted evenly and reduces the possibility of a tilting of insert 14 with respect to dish 12 during operation.

As earlier noted, the fully raised position of insert 14 is defined by the interaction of beads 28 of sidewall segments 24 and annular bead 32 of upstanding wall 18. The fully raised position of insert 14 is also defined by interaction of cam 56 with raised portion 58 of dish bottom 16. Cam 56 has a stop 60 near opposite end 52 of lever 46. Stop 60 is engageable with the outer edge 62 of raised portion 58 to stop further depression of upper depression surface 54 when insert 14 reaches its fully raised position. This interaction serves to prevent insert 14 from being accidentally detached from its nested relationship with dish 12.

In use, dispenser 10 will typically rest on a substantially horizontal surface. When insert 14 is fully nested with shallow dish 12, the outflow of air-treating vapors will be minimized. To start or increase the flow of air-treating vapors, the operator pushes downwardly on upper depression surface 54 to raise insert 14 to its fully raised position or to some intermediate position as desired. When insert 14 is elevated, air currents will flow through apertures 26 and over and under volatile material 40 to increase the volatilization of the air-treating composition and to provide an outflow of air-treating vapors. To partially or completely close dispenser 10, the operator simply pushes downwardly on cover 20.

Shallow dish 12 is preferably made of plastic, using well known plastic forming methods. Insert 14, lever 46, and hinge 50 are preferably an integral plastic piece, also formed using well known plastic forming methods.

While in the foregoing specification, this invention has been described in relation to certain preferred embodiments and many details have been set forth for purpose of illustration, it will be apparent to those skilled in the art that the invention is susceptible to additional embodiments and that certain of the details described herein can be varied considerably without departing from the basic principles of the invention.

I claim:

1. A dispenser for air-treating vapors comprising:
   a shallow dish having a bottom and a surrounding upstanding wall;
   an insert nested within the dish and having a cover and a plurality of sidewall segments adjacent to said wall and defining apertures therebetween, said cover defining a lever opening;
   a lever within the opening hinged at one end to the cover and having an upper depression surface at its opposite end, said lever having a lower fulcrum in contact with said bottom midway between the lever ends, whereby depression of said depression surface raises the insert from its fully nested position to expose the apertures above the upstanding wall; and
   a volatile air-treating material between said bottom and said cover.

2. The device of claim 1 wherein said depression surface is adjacent to the wall and said hinge is remote from the wall whereby to provide a substantially centrally located lift point for the insert.

3. The device of claim 2 wherein said fulcrum comprises a convex cam about which the lever rotates as it is depressed.

4. The device of claim 3 wherein said bottom has a raised portion engaging the cam and the cam has a stop near said opposite end engageable with the raised portion to stop further depression of the lever when the insert reaches its fully raised position.

5. The device of claim 1 wherein the depression surface and cover are substantially coplanar.

6. The device of claim 1 wherein the upstanding wall and the sidewall segments have interacting means to prevent further raising of the insert in its fully raised position.

7. The device of claim 1 wherein the sidewall segments have support means for suspending a layer of said volatile material beneath the cover.

8. The device of claim 1 wherein the insert, lever, and hinge are an integral plastic piece.

9. A device for dispensing air-treating vapors from a volatile air-treating material, comprising:
   a lower member with an open top;
   an upper member with an open bottom and nested with the lower member, said upper member being movable with respect to the lower member between a fully nested position enclosing said volatile material and a raised position exposing said volatile material;
   a lever hinged at one end to the upper member and having an upper depression surface at its opposite end, said lever having a lower fulcrum in contact with said lower member midway between the lever ends, whereby depression thereof raises the upper member from its fully nested position to its raised position.

10. The device of claim 9 wherein said fulcrum comprises a convex cam about which the lever rotates as it is depressed.

* * * * *